United States Patent [19]
Chen et al.

[11] Patent Number: 5,654,266
[45] Date of Patent: Aug. 5, 1997

[54] COMPOSITION FOR TISSUES TO SUSTAIN VIABILITY AND BIOLOGICAL FUNCTIONS IN SURGERY AND STORAGE

[76] Inventors: Chung-Ho Chen; Sumi C. Chen, both of 13704 Killarney Ct., Phoenix, Md. 21131

[21] Appl. No.: 218,109

[22] Filed: Mar. 28, 1994

Related U.S. Application Data

[63] Continuation-in-part of Ser. No. 833,027, Feb. 10, 1992, Pat. No. 5,298,487.
[51] Int. Cl.⁶ .......................... A61K 31/22; A61K 38/00
[52] U.S. Cl. ........................ 514/2; 514/21; 514/546; 514/912
[58] Field of Search ........................ 514/2, 912, 21, 514/546

[56] References Cited

U.S. PATENT DOCUMENTS 5,298,487   3/1994   Chen et al. ..................... 514/2

*Primary Examiner*—Zohreh Fay
*Attorney, Agent, or Firm*—Cushman Darby & Cushman, L.L.P.

[57] ABSTRACT

A composition composing ketone bodies and/or precursors thereof and an aqueous phosphate-buffered balanced salt solution with citrate, $HPO_4^{-2}$ and $Ca^{2+}$ in a defined concentration ratio, and methods, including a mechanism and an associated set of protocols, to make the solution without causing autoclave-elicited caramelization and precipitation in the manufacturing process are disclosed. The disclosed composition is particularly useful as a rich energy source for isolated tissue and for peripheral tissues under surgery with concurrent suppression of lactic acid formation and accumulation in the cells. It may be used in ocular surgery and surgeries in general, although other uses, for example, topical application and storage and rinsing of donor tissues prior to transplantation are also contemplated.

23 Claims, No Drawings

COMPOSITION FOR TISSUES TO SUSTAIN VIABILITY AND BIOLOGICAL FUNCTIONS IN SURGERY AND STORAGE

This application is a Continuation-in-Part application of Ser. No. 07/833,027 filed Feb. 10, 1992, now U.S. Pat. No. 5,298,487.

BACKGROUND OF THE INVENTION

1. Technical Field

The present invention relates to a novel composition having a built-in mechanism that utilizes citrate, $Ca^{2+}$ and $HPO_4^{-2}$ in a defined ratio and a specific protocol capable of preventing autoclave-elicited precipitation and caramelization in the manufacturing process. The composition is particularly useful as a rich energy source for ocular tissues under surgery, with concurrent suppression of lactic acid formation and accumulation in the cells. It may be used in surgeries in general, although other uses, for example, tissue storage and preparation for grafting, and topical application are also contemplated.

2. Background Information

The present invention is distinctly different from the prior art (Chen, et al., U.S. Pat. No. 5,116,868). Specifically, it contains no glucose and has a built-in mechanism that utilizes citrate, $Ca^{2+}$ and $HPO_4^{-2}$ in a defined ratio, together with a specific protocol that includes heating the solution under vacuum, followed with rapid cooling, to prevent autoclave-elicited precipitation.

Sterilization is an essential element in the manufacturing process. Heat sterilization after closing (sealing the container) is preferred by the pharmaceutical industry for safety reasons. Filtration, which proceeds before closing, is considered risky although it is acceptable to the Food and Drug Administration for sterilizing solutions that contain heat-labile components.

Filtration as a sterilization means was used in the prior art (Chen, et al., U.S. Pat. No. 5,116,868) because the medium contains 5.5 mM glucose, pH 7.4, which is known to caramelize when heated. In addition, however, it is discovered that autoclave manifests not only caramelization, but also precipitation. These problems have rendered the composition unacceptable to the pharmaceutical industry despite its efficacy.

The source of precipitation was traced to calcium salts, and a mechanism means was discovered to overcome the precipitation problem. It is indispensable for solutions containing $HPO_4^{-2}$ and $Ca^{+2}$ to be heat sterilized. It is also useful for manufacturing solutions that contain 5.5 mM glucose at pH 7.4 without caramelization. The rationale for the latter is not fully understood, but is probably attributable to the $O_2$-free environment.

The discovery of a means to prevent autoclave-elicited precipitation and caramelization in the manufacturing process is a significant scientific as well as technological achievement. There was no hint in prior arts as to how to overcome these problems. Prior to applicant's invention, in order to autoclave, $Ca^{2+}$ and $HPO_4^{-2}$ have to be separated and glucose had to be present in high concentrations, about 5%–10% or 275 mM–550 mM, at acidic pH (around 5.0). These conditions are non-physiological accordingly harmful to tissues. For instance, in the methods of Garabedian, et al. (U.S. Pat. Nos. 4,443,432 and 4,550,022), the ophthalmic irrigating solution (trade name BSS-plus, marketed by Alcon, Fort Worth, Tex.) is manufactured by separating $Ca^{2+}$ from phosphate and $NaHCO_3$ in two bottles and by using filtration to sterilize the small bottle that contains 5.1 mM glucose.

The present use of citrate is distinctly different from the prior art (Chen, et al., U.S. Pat. No. 5,116,868), where citrate is employed as an antioxidant for protecting $\beta$-hydroxybutyrate from oxidation because the solution is not $O_2$-free. Because of this use, citrate can be replaced by one or more of antioxidants such as glutathione, vitamin E and ascorbate. Whereas, in this novel mechanism, citrate is added to prevent autoclave-elicited precipitation, and citrate can be replaced by isocitrate, another tricarboxylic acid, but not antioxidants.

The complete effect of citrate is not fully understood. Solubility of calcium salts is not a sole determining factor, because di- and mono-carboxylic acids such as oxaloacetate, maleate, fumerate, succinate, malate, and acetate form more soluble calcium salts, but are not as effective (see Table 1). These acids have to be present in about 10–20 times higher concentrations and even then are only effective to prevent precipitation up to 90° C.

The composition of the prior art contains 10 mM citrate, 20 mM acetate, 2 mM $Ca^{2+}$, 5 mM $HPO_4^{-2}$, and 5mM $H_2PO_4^{-1}$. Table 1 shows that $Ca^{2+}$ salts of these anions, except $HPO_4^{-2}$, are within soluble ranges. The $[Ca^{2+}][HPO_4^{-2}]$ value (10.0) is greater than the solubility product at 38° C. ($[Ca^{2+}][HPO_4^{-2}]=(1.8)^2=3.24$) and less than that at 100° C. (19.36). According to the solubility theory, the solution should precipitate (as $CaHPO_4$) at room temperature, but clear at $\geq$100° C. However, since it is clear at room temperature, the level of free $Ca^{2+}$ must has been reduced to <0.65 mM through chelation with anions. Occurrence of precipitation at elevated temperatures is thus inconsistent with both the solubility and free $Ca^{2+}$ theories, and is therefore totally unexpected.

TABLE 1

Solubility of Selected Calcium Salts

| Anions | Solubility (mM) | |
|---|---|---|
| $H_2PO_4^{-1}$ | 71.4 (30° C.) | |
| $HPO_4-2$ | 1.8 (38° C.), | 4.4 (100° C.) |
| Acetate | 2364.5 (0° C.), | 1877.7 (100° C.) |
| Citrate | 14.9 (18° C.), | 16.8 (23° C.) |
| Fumarate | 101.4 (30° C.) | |
| Malate | 39.0 (0° C.), | 58.8 (37.5° C.) |
| Maleate | 167.9 (25° C.), | 186.5 (40° C.) |
| Malonate | 20.5 (0° C.), | 33.6 (100° C.) |
| Succinate | 9.1 (10° C.), | 41.9 (80° C.) |

Re-calculated from data in Handbook of Chemistry and Physics, R. C. Weast, editor, 49th ed., the Chemical Rubber Co., Cleveland, OH, pp. B-185–B-188, 1968.

Glucose, a major energy source for mammalian cells, is used in the irrigating solutions of prior arts to mimic in vivo conditions. However, it is discovered that under surgical conditions the cells of vascularized tissues continue to extract glucose from the blood circulation; whereas, those of avascular tissues use endogenous glucose from glycogen (a glucose storage in vivo) when glucose is absent in the irrigating solution. In addition, in the presence of $\beta$-hydroxybutyrate, glucose metabolism, and thus lactate production, are reduced. Duration of endogenous glucose availability is thus extended, which ranges from several hours to several days depending on glycogen storage levels. Therefore, exogenous $\beta$-hydroxybutyrate is adequate to serve as an energy source for tissues to sustain their viability and to perform physiologic functions in ocular and other short term surgeries.

With the novel mechanism, the present composition is able to combine with many other components for specific applications, such as the additions of glucose for application in lengthy surgery and perfusion if desired, of polymers to form a slow-release drug delivery system, and of essential components selected from Medium 199 for optimal corneal storage.

Utilization of the viscous solution as a slow-release drug delivery vehicle is an unique and novel concept. Diffusion rate of solutes in viscous solutions is markedly reduced and the high viscosity will extend the duration of the solution's contact with tissues. When drugs such as antibiotics, steroids and other medications for treating eye diseases and polysaccharides are incorporated into the present composition, duration of pharmacological action of drugs is extended and side effects are reduced.

When applied in the anterior chamber, the high viscosity of the solution will reduce the aqueous flow and thus hinder corneal endothelium and lens epithelium from obtaining nourishment from the aqueous solution. Similarly, when applied on the external surface of the eye, it hinders corneal epithelium from obtaining nourishments from tears. The presence of β-hydroxybutyrate in the composition overcomes these problems. Namely, β-hydroxybutyrate effectively meets the requirements for the ocular tissues to sustain viability and to perform physiologic functions with concurrent suppression of lactate production and accumulation.

The present isotonic medium is very effective for corneal storage and for preserving corneal endothelium for both humans and animals. Specifically, $Fe(NO_3)_3$, ascorbate and $NaHCO_3$ are omitted to prevent the formation of free radicals and $H_2O_2$ and the shifting of pH from 7.4 to alkaline values when exposed to air. In addition, while the medium is kept isotonic, $Cl^-$ level is reduced from 145 mM to 90 mM and polysaccharides and glucuronate are added to minimize the corneal swelling related to $Cl^-$ passive accumulation and the loss of stromal extracellular matrix substances during storage. When stored in this isotonic medium, stored cornea is are able to perform deturgescence function without resorting to dehydrating agents to maintain the desired thinness.

The specific features of the isotonic medium of the invention are lacking in the prior art. In one method described by Chen, et al. (U.S. Pat. No. 4,873,186), β-hydroxybutyrate is added to Medium 199, which contains $NaHCO_3$, $Fe(NO_3)_3$ and ascorbate. In another method described by Chen, et al. (divisional application of U.S. Pat. No. 5,116,868), a corneal storage medium is formed by replacing the balanced salt solution of a tissue culture medium with ophthalmic irrigation solution. Both media are hypertonic, up to 370 mOsM, and are effective in storing rabbit corneas for only up to 5 days at 4° C. This is about 50% as effective as the isotonic medium of the present invention. In addition, they do not employ agents such as glucuronate and polysaccharides and a reduced $Cl_-$ level to minimize corneal swelling.

The theory and intended application of polysaccharides and glucuronate for corneal storage are distinctly different from those of dextran and chondroitin sulfate described by Lindstrom, et al. (U.S. Pat. No. 4,695,536 and *Am. J. Ophthalmol.*, 95, 869, 1977) and McCarey, et al. (*Invest. Ophthalmol.*, 13, 165, 1974). These articles describe tissue culture techniques that scientists in the field have been using for years, except for the addition of chondroitin sulfate and/or dextran to exert a colloid osmotic pressure on stored corneas under hypertonic conditions thereby achieving an artificial dehydrating effect. In addition, $NaHCO_3$, $Fe(NO_3)_3$ and ascorbate are present in these storage media.

It is believed that deturgescence of the cornea is mediated by fluid and ion transports located in the endothelium with energy derived mainly from glucose. Forty-seven percent of the energy is derived from the glycolysis pathway where the pyruvate formed is reduced to lactate at the expense of NADH, an intracellular high energy reserve (Chen, et al., *Arch. Biochem. Biophys.*, 276, 70, 1990). Glycolysis is not generally an energy-efficient pathway, since only 2 moles of ATP are formed per mole of glucose utilized.

It is important to note that lactate is not toxic. In fact, lactate is utilized in vivo in tissues such as the liver and heart. Exogenous lactate is also utilized in the cornea (Kuhlman, et al., *Arch. Biochem. Biophys.*, 85, 29, 1959). However, when pyruvate and lactate are formed in the cells from glucose, two equivalents of $H^+$ are generated. $H^+$ produced normally is removed via mechanisms such as facilitated $H^+$-lactate symport (Spencer, et al., *Biochem. J.*, 154, 405, 1976) and $H^+/Na^+$ antiport (Knicklebein, et al., *Am. J. Physiol.*, 245, 504, 1983), with subsequent clearance, accompanying the lactate through the blood circulation. A clearance mechanism is lacking in tissues under storage and in cell cultures, and is ineffective in tissues under surgery. Under these conditions, glucose metabolism may lead to excessive accumulation of lactic acid outside the cells. This, in turn, inhibits $H^+$-lactate symport, which results in cellular acidity with subsequent inhibition of tissue metabolic function (Chen, et al., *Arch. Biochem. Biophys.*, 276, 70, 1990).

Ketone bodies are a collective term for β-hydroxybutyrate ($CH_3CHOHCH_2COO^-$), acetoacetate ($CH_3COCH_2COO^-$) and acetone ($CH_3COCH_3$). Ketone bodies, they are readily generated from fatty acids and ketogenic amino acids (such as phenylalanine, leucine, lysine, tryptophan, and tyrosine), with the major metabolic site being in the liver. Among these, acetone is not metabolized and is excreted via breath, sweat and urine. Whereas, acetoacetate and β-hydroxybutyrate are delivered to peripheral tissues for storage or catabolism to generate energy.

Ketone bodies and precursors thereof are efficient energy-rich metabolites, not metabolic wastes. They are synthesized during development (Drahota, et al., *Biochem. J.*, 93, 61, 1964) and in a physiologic response when glucose is inadequate or lacking. For instance, they are elevated in the blood under diabetic conditions and in non-diabetic man following extended fasting. Ketone bodies are the preferred fuel for the brain, muscle, and kidney during starvation (Olson, *Nature*, 195, 597, 1962; Bassenge, et al., *Am. J. Physiol.*, 208, 162, 1965; Owen, et al., *J. Clin. Invest.*, 46, 1589, 1967; and Howkins, et al., *Biochem. J.*, 122, 13, 1971 and 125, 541, 1971). They are readily oxidized in peripheral tissues, yielding 32 molecules of ATP per acetyl moiety utilized. In addition, the enhanced respiration will inhibit glycolysis via the Pasteur effect (Krebs, *Essays Biochem.*, 8, 1, 1972), thus reducing lactic acid formation and accumulation.

The $NaHCO_3$ as high as 25–30 mM is reportedly needed for the cornea to deturgesce in vitro (Hodson, et al., *J. Physiol.*, 263, 563, 1976). However, oxidation of β-hydroxybutyrate is able to generate adequate $HCO_3^-$ for the cornea to perform physiologic functions in vivo normally (Chen, et al., *Transplantation*, in press, 1994), thus enabling omission of $NaHCO_3$ from the irrigating solution. This resembles the built-in $HCO_3^-$-generating system that exists in humans and animals in vivo, in which $HCO_3^-$ is generated from oxidation of ingested foods, not $NaHCO_3$ contained in the foods.

The present composition without $NaHCO_3$ has a stable pH and is favorable for clinical applications. When solutions containing $NaHCO_3$ are used, it requires a calculated $P_{CO2}$ to maintain the designated pH's. This can be done in a closed system, such as in vitro experiments. However, in an open system, such as that in surgery and in donor tissue preparation for transplantation, $P_{CO2}$ is low and variable. Consequently, the pH of $HCO_3^-$-containing solutions, such as BSS-plus and McCarey-Kaufman medium, will shift to become alkaline when opened to air, which also causes $Ca^{2+}$ to precipitate. According to the manufacturer, BSS-plus has to be discarded after mixing for four hours. It has no mechanisms to prevent precipitation.

The theory and intended application of the present composition differ from the teaching of Veech (U.S. Patent No. 4,663,289). In the teaching of Veech, β-hydroxybutyrate has to be coupled to acetoacetate in a defined ratio, and β-hydroxybutyrate is not intended to use as a high energy source for ocular and peripheral tissues and to inhibit lactate production and accumulation. Veech's invention is based on the theory that the metabolic process in living animal cells can be regulated by a medium containing one or more of the $[HCO_3^-]/[CO_2]$, [β-hydroxybutyrate]/[acetoacetate], and $[L\text{-lactate}^-]/[\text{pyruvate}^-]$ couples in defined ratios. This parallels the buffer system of the "weak acid/conjugated base" couple in regulating pH. Veech's invention is based on several assumptions:

1. Both of the coupled-substrates in a defined ratio in the medium are taken up together by tissues, and remain there at the same ratio to regulate the metabolic process.
2. Uptake and metabolic regulation of these coupled substrates for all tissues are same.

Much of the experiments, on which Veech based his invention, were done with the rat liver (Veech, et al., *Biochem. J.*, 115, 609, 1969 and *J. Biol. Chem.*, 254, 6538, 1979). In humans and animals, the liver is the metabolic center, and it differs from peripheral tissues in the metabolic process. Therefore, the mechanism for regulating the metabolic process in the liver, may not necessarily work in peripheral tissues. For example, although ketone bodies are synthesized in the liver, they are not utilized there, but rather are translocated to peripheral tissues via the blood circulation. There, they are oxidized to yield a high level of ATP (Principles of Biochemistry, Lehninger, Worth Publishers, Inc.). Thus, β-hydroxybutyrate serve as an efficient fuel for peripheral tissues, but not for the liver.

In addition, the substrate-couples are interchangeable. Whenever one of the metabolites is taken up or produced in the cells, another substrate of the couple is formed. The isozymes of dehydrogenases catalyzing these reactions vary from tissue to tissue. Those in the liver catalyze the reactions towards oxidation; whereas those in peripheral tissues favor reduction. Because of tissue-dependent variations in isozymes and of constant changes in metabolite levels in vivo due to factors such as fluxes, metabolism and food-intakes, it is difficult to establish a generalized ratio for substrate-couples, such as those described by Veech, for all tissues.

SUMMARY OF THE INVENTION

The present invention relates to a novel composition comprising ketone bodies and/or precursors thereof in an aqueous phosphate-buffered balanced salt solution, that effectively meets the requirements of tissues under storage or surgeries for efficient physiologic and biochemical functions, as detailed above. The present invention also relates to a built-in mechanism that utilizes citrate, $HPO_4^{-2}$ and $Ca^{2+}$ in a defined concentration ratio, together with a specific set of sequential procedures, to prevent autoclave-elicited precipitation and caramelization in the manufacturing process.

DETAILED DESCRIPTION OF THE INVENTION

Broadly described, the composition of the present invention comprises ketone bodies and precursors thereof and a citrate-containing phosphate-buffered balanced salt solution. It utilizes certain of the special features of its components, particularly ketone bodies and/or precursors thereof as detailed above, so as to effectively meet the requirements of ocular and other peripheral tissues to sustain viability and to perform physiologic functions during surgery and the transitional period that follows, until a full equilibration of the solution with physiologic body fluids. It is also useful for skin and ophthalmic topical applications, for storage and rinsing of donor tissues prior to transplantation, and for surgeries in general.

The composition also utilizes certain of the special features of its components, particularly $HPO_4^{-2}$, $Ca^{2+}$ and citrate in a defined ratio, together with a specific set of sequential procedures, so as to form a built-in mechanism to prevent autoclave-elicited precipitation and caramelization in the manufacturing process.

Table 2 summarizes components, including ranges, of a typical composition which is suitable for use as an irrigating solution according to the present invention. The calculated osmolarity of the composition is 328.5 mOsM, with ranges from 315 to 345 mOsM, if all the salts are fully dissociated. The actual osmolarity of the prepared solution of the present composition is about 302 mOsM, or actual in the range from about 290 to about 315 mOsM.

TABLE 2

TYPICAL COMPOSITIONS OF THE INVENTED SOLUTION

| | Concentrations | | |
|---|---|---|---|
| Components | mg/ml | mM | Ranges |
| D,L-Sodium β-Hydroxybutyrate | 1.51 | 12 | 5–30 |
| Potassium Chloride | 0.75 | 10 | 5–20 |
| Sodium Chloride | 7.71 | 132 | 95–135 |
| Dibasic Sodium Phosphate (heptahydrate) | 0.67 | 2.5 | 1.5–6.0 |
| Monobasic Sodium Phosphate (monohydrate) | 0.07 | 0.5 | 0.3–1.2 |
| Sodium Citrate (dihydrate) | 0.59 | 2.0 | 1.2–7.2 |
| Magnesium Chloride (hexahydrate) | 0.24 | 1.2 | 0.5–1.5 |
| Calcium Chloride (anhydrate) | 0.09 | 0.8 | 0.5–2.0 |

The solution is prepared in sequential orders:

First, all ingredients, except $CaCl_2$ and $MgCl_2$, are dissolved and thoroughly mixed in deionized, double-distilled and de-gassed $H_2O$, preferably 90%–95% of total volume; and the pH is checked and adjusted to 7.3–7.4 with 1N HCl or NaOH as needed. Second, $CaCl_2$ and $MgCl_2$ are added and mixed, followed with $H_2O$ to make up the volume, and the pH is re-adjusted as needed. Third, the solution is filtered through 0.22 μm membrane (Nalge Co., Rochester, N.Y.), bottled and sealed under vacuum to insure a complete elimination of $O_2$ from the solution to protect β-hydroxybutyrate from oxidation and to extend the shelf-life. And fourth, the solution is sterilized by autoclave or showers of super-heated water at 121°–123° C. for 15–20 min, and immediately cooled rapidly with showers of water in two stages to prevent breakage of glass bottles, first at 60° C. or between 50° C. and 80° C. depending on quality of bottles used and then at 4° C. until the precipitates disappear.

Cooling also can be achieved by immersing in a water bath at appropriate temperature ranges. A stream of cold air may be used at the first stage, but not as effective.

The rapid cooling step is critical and important; it enables the fine crystals formed under autoclave to re-dissolve into the solution prior to settlement. Without this step, the crystals will grow in sizes while settling down to the bottom of the container and will be very difficult to re-dissolve.

The de-gassing and vacuum processes prior to sterilization by heat are also critical and important; it enables 5.5 mM glucose to be added the present composition without causing autoclave-elicited caramelization.

A number of variations are possible when preparing the present irrigating solution. Some examples of possible variations are given below.

1. The phosphate buffer can be prepared using di- and monobasic potassium phosphate salts and phosphoric acid, with titration to pH 7.4 and adjustment of KCl to 10 mM.

2. Sodium salts of one or more ketogenic amino acids at concentrations from 0.1 to 5.0 mM, preferably 1 to 2 mM, can be added with an appropriate adjustment of NaCl concentration.

3. β-Hydroxybutyrate can be replaced by acetoacetate. However, β-hydroxybutyrate, a stable and cost-efficient metabolite, is preferred.

4. The D-isomer of β-hydroxybutyrate is preferred because only D-isomer is utilized in the cells. However, D, L- racemate or isomer mixtures are cost-efficient and readily available commercially, and can be used.

5. Citrate can be replaced by isocitrate.

6. Potassium salts of β-hydroxybutyrate and citrate (or isocitrate) can be used, with appropriate adjustment of KCl and NaCl concentrations.

7. If necessary, disaccharides such as mannitol and sucrose or neutral polysaccharides such as dextran can be used to adjust the osmolarity of the solution to 300 mOsM or in the ranges of about 290 to 315 mOsM.

The present composition contains a physiologically compatible salt solution, with concentration ranges similar to those in the plasma. According to the present invention, phosphate serves as a buffer, as well as a substrate for oxidative phosphorylation. It has a strong buffer capacity at the physiologic pH ranges, from pH 7.2 to 7.4. Concentrations of $HPO_4^{-2}$, $Ca^{2+}$, and citrate may vary, but are kept at the defined ratio. Typically, the $[HPO_4^{-2}][Ca^{2+}]$ value is 2.0, or ranging from 1.2 to 3.2, and concentration of citrate is about 80% that of $[HPO_4^{-2}]$, or in the range from 50% to 120%. The $[HPO_4^{-2}]/[H_2PO_4^{-1}]$ ratio is at 5:1 to achieve a pH of 7.3–7.4.

With its unique energy-efficient and autoclave-friendly features, the novel composition is favorable for incorporation of many other ingredients for various specific applications.

According to one embodiment, glucose at 5.5 mM is added for applications in extended perfusion of tissues and in lengthy surgeries if desired.

In a second embodiment, an isotonic medium, without $NaHCO_3$, $Fe(NO_3)_3$ and ascorbate, is prepared by combining the present composition with glucuronate, Hepes (N-2-hydroxyethylpiperazine-N-2-ethanesulfonic acid), glucose, dextran and pre-formulated essential amino acids, vitamins and other components of Morgan, et al. Medium (*Proc. Soc. Exp. Biol. Med.*, 73, 1, 1950). NaCl is reduced from 137 mM to 76 mM to adjust the osmolarity to 300 mOsM, or ranging from 290 to 315 mOsM. Antibiotics can be added as needed. The isotonic medium is especially effective for extended storage and preparation of donor tissues for transplantation. A hypertonic medium also can be used, but not as effective. Typical composition, with concentration ranges, is shown in Table 3. Among them, glucose and β-hydroxybutyrate form a balanced energy source for long term storage of donor tissues. Glucuronate may be replaced with a member of glucosaminoglycan moieties including N-acetyl glucosamine, gluconate, mannuronate, galacturonate and glucarate. Dextran with molecular mass of 40,000 daltons is preferable, but those with higher molecular masses, such as 70,000 daltons, are also effective. The isotonic medium has a pH of 7.3–7.4, with buffer capacity strengthened by 30 mM Hepes and 3 mM phosphate buffers.

TABLE 3

Typical Compositions Of Isotonic Medium For Donor Tissues

| Components | Concentration | | |
|---|---|---|---|
| | mg/ml | mM | Ranges |
| D,L-Sodium β-Hydroxybutyrate | 1.26 | 10 | 5–30 |
| Glucose | 1.00 | 5.5 | 2–10 |
| Sodium Glucuronate | 2.16 | 10 | 5–20 |
| Dextran | 70.00 | 7 (%) | 4–15 (%) |
| Pre-formulated essential Amino Acids, Vitamins and Other components | | (full strength) | |
| Sodium Hepes | 7.48 | 30 | 10–50 |
| Potassium Chloride | 0.75 | 10 | 5–20 |
| Sodium Chloride | 4.42 | 75.6 | 60–100 |
| Dibasic Sodium Phosphate (heptahydrate) | 0.67 | 2.5 | 1.5–6.0 |
| Monobasic Sodium Phosphate (monohydrate) | 0.07 | 0.5 | 0.3–1.2 |
| Magnesium Chloride (hexahydrate) | 0.24 | 1.2 | 0.5–1.5 |
| Calcium Chloride (anhydrate) | 0.09 | 0.8 | 0.5–2.0 | pH is adjusted to 7.4 with HCl or NaOH.

Pre-formulated minimal essential amino acids and vitamins of either Eagle's (*Science*, 130, 432, 1959), Dubelcco's (*Virology*, 8, 396, 1959) or Daniel's (*Proc. Soc. Exp. Biol. Med.*, 127, 919, 1968) can be used. They are commercially available. Because vitamins in general are heat-labile, the medium has to be sterilized by filtration using 0.22 μm filter, kept cold and used within about 24 months. It is not necessary, although helpful, to use de-gassed $H_2O$ for making the medium. As heat-sterilization is no longer needed, citrate is omitted.

In a third embodiment, portion of NaCl in the second embodiment described above is replaced with the synergistic composition described in the teaching of Chen, et al. (U.S. Pat. No. 5,073,492), with the medium remains isotonic, pH 7.3–7.4. The synergistic composition consists essentially of a synergistically effective mixture of vascular endothelial growth factor (VEGF), 10 μM uridine, 0.5 μM thymidine and serum-derived factor (SDF). Typically, dialyzed fetal bovine retinal extract (0.1 mg/ml) and dialyzed fetal bovine serum (3 mg/ml) are used as the sources of VEGF and SDF, respectively. This isotonic medium is especially effective for perfusion of vascularized donor organs, such as the heart and kidney, through the vasculature, in preparations for organ transplantation.

In a fourth embodiment, glucuronate and dextran in the composition of the second or third embodiments described above are replaced with 15 mM $NaHCO_3$, with osmolarity maintained at actual 310–320 mOsM by adjusting NaCl concentration. The medium is especially effective for cell cultures when it is used under a humidified air containing 5% $CO_2$.

In a fifth embodiment, a slow-release drug delivery mechanism is prepared by replacing portion of NaCl in the composition of the first embodiment with polymers, preferably molecular mass $\geq 5 \times 10^5$ daltons, such as dextran, hydroxypropyl methylcellulose, hyaluronate and polyvinyl pyrrolidone at 1% or ranging from 0.5% to 5%. The ratio is 1% of polymers for 2.5 mM NaCl. When medications such as antibiotics, steroids, and drugs for treating eye conditions are incorporated, the viscous solution is especially effective to extend the duration of pharmacological actions with reduced side effects, while it provides the eye tissues with high energy metabolites to sustain viability and to perform physiologic functions, with concurrent suppression of lactate formation and accumulation.

In a sixth embodiment, the composition of the first embodiment is combined with the ophthalmic antibiotics and/or steroid ointment for treating eye conditions as intended, while it extends the duration of pharmacological actions and provides the eye tissues with high energy metabolites to sustain viability and to perform physiologic functions, with concurrent suppression of lactate formation and accumulation.

In a seven embodiment, the composition of the first embodiment is combined with antibiotics and/or steroids ointment or cream for external applications to treat skin conditions as intended, while it provides dermal cells with high energy metabolites to sustain viability and to perform physiologic functions, with concurrent suppression of lactate formation and accumulation.

The present invention will be illustrated in details in the following examples. The examples are included for illustrative purposes and should not be considered to limit the present invention.

EXAMPLE 1

The present composition, as exemplified in Table 2, was used for experiments. Variations in concentrations of these components within the ranges as indicated in Table 2 are similarly effective. Efficacy of the solution was compared to BSS-plus, which contains glutathione, a tripeptide reportedly beneficial for corneal fluid transport (Dikstein, et al., *J. Physiol.*, 221, 29, 1972). BSS-plus is one of the most widely used ophthalmic irrigating solutions.

According to the procedure of the experiment (Chen, et al., *Transplantation*, in press, 1994), under anesthesia a 2 mm incision on the lower temporal side of cat cornea was made, and 0.35 ml of heparin (1,000 units/ml) was injected into the anterior chamber to prevent fibrin formation. An 18-gauge catheter connected to a bottle containing testing solution was carefully inserted, about 3 to 4 mm, through the incision. The infusion was commenced with a 4-mm incision on the upper nasal side of the cornea. A hydrostatic pressure was maintained at 25–28 cm, yielding a flow rate of about 1.0–1.5 ml/min for a total of about 2 hours. Following infusion, 0.15 ml of heparin was injected into the anterior chamber. Then, the incisions were closed with 10-0 monofilament nylon sutures, followed by a subconjunctival injection of 0.15 ml dexamethasone phosphate (4 mg/ml). Gentamicin eye drops were instilled once a day for one week.

For comparative purposes, the identical procedure was performed with the only exception being the uses of the present composition in one case, and BSS-plus in other cases. Prior to infusion and at appropriate intervals thereafter, the endothelium was photographed and corneal thickness was measured using a specular microscope with a built-in digital pachymeter. Density of endothelial cells was estimated from the photographs.

After infusion with the present composition, there are no remarkable changes in both endothelial cell density and corneal thickness over a period of 60 days post-operatively. In sharp contrast, when infused with BSS-plus, the cornea swelled about 21% within 2 days ($P<0.01$). A thinning effect was not observed until about 3 weeks after infusion. Accompanying these changes, the endothelial cell density decreased about 18% ($P=0.02$) within 20 days and about 25% ($P=0.01$) in 60 days after grafting. The elicited swelling effect precedes the endothelial cell loss, indicating that some of affected cells do not survive after infusion.

Following infusion with the present composition, the endothelium retained its hexagonal characteristic morphology with homogeneity in cell sizes. In contrast, in the experiments with BSS-plus, swelling and polymorphism of corneal endothelial cells are clearly evident when examined on day 2 and day 30, respectively.

The above results show that, determined on the basis of endothelial integrity, the present composition is more effective than BSS-plus. Furthermore, the cat cornea performs physiologic function normally when the present composition is used. It is further noted that in this animal experiment, the continuous infusion of the testing solution into the anterior chamber was performed over a period of time much longer than that of ocular surgery under normal conditions. It is therefore concluded that the present composition has an efficacious effect on ocular tissues in clinical applications.

EXAMPLE 2

It is known that the cornea swells when kept at 4° C. because of inadequate energy out-put for pumping fluid and ions, and deswells when the temperature is raised. Deturgescence activity of isolated corneas based on the temperature reversal process is therefore a measurement of the barrier, fluid pump and metabolic functions of the cornea, as well as the efficacy of exogenous metabolites for the cornea to perform these functions.

According to the procedure of the experiment, New Zealand albino male rabbits, weighing 2.5 to 3.0 kg, were killed by an overdose cardiac injection of pentobarbital, and kept in a cold room at 4° C. with eyes taped shut for 20 hours to induce corneal swelling. The cornea with a 1.5 mm scleral rim was excised and incubated in the testing solution at 34° C. in a Cooper Vision viewing chamber. Corneal thickness was measured at time intervals using a digital pachymeter attached to a specular microscope.

For comparative purposes, the identical procedure was performed, with the only exception being the incubation, in one case, in the present composition as exemplified in Table 2, and in another case, in BSS-plus.

Isolated rabbit cornea deturgesces rapidly at 34° C. in the present composition, completing the thinning process in about 20–30 minutes with a rate estimated at about 236.0±19.8 μm/hr (N=6). When incubated in BSS-plus, the cornea exhibits a considerably lower thinning rate, estimated at about 195.9±13.1 um/hr N=6), and it took a longer time to complete the thinning process, about 40–50 minutes. The results indicate that the tissue performs physiologic functions more efficiently in the present composition than in BSS-plus.

EXAMPLE 3

In general, isolated corneas swell during storage at 4° C. When grafted to a recipient, the grafts using donor corneas with well-preserved viability, metabolic activity and endothelium fluid pump function will deturgesce at high rates, and clarity of the graft is readily attainable. Otherwise, the grafts will deturgesce at lower rates, or even swell after grafting. Efficacy of the present isotonic medium, as exemplified in Table 3, was evaluated on the basis of this property.

According to the procedure of the experiment, New Zealand albino male rabbits, weighing 3.0 to 3.5 kg, were killed and the corneas with 1.5 mm scleral rims were isolated. For comparative purposes, one of the corneas from the same donor was stored in the present isotonic medium and another in the hypertonic Optisol (marketed by Chiron, Irvine, Calif.), one of the most widely used corneal storage media at the present time. After storage for, in one case, 7 days and, in another case, 11 days, a 7.5 mm donor corneal button was cut with a trephine and grafted to a recipient rabbit. The grafting procedure took about 30–45 minutes. Donor corneal thickness was measured immediately after grafting, and at appropriate intervals thereafter.

The grafts using donor corneas stored in the present isotonic medium for 7 days deturgesce rapidly, with a short half-time ($t_{1/2}$) to return to the normal thickness of about 340–370 μm. The grafts using donor corneas stored for 11 days deturgesce at about 1/12th of rates, with about 14 times longer in $t_{1/2}$.

In sharp contrast, the grafts using donor corneas stored in Optisol for 7 and 11 days, respectively, swell for about 3 and 5 hours, and then deswell at negligible rates with a very long $t_{1/2}$. Deturgescence rates and $t_{1/2}$ of grafts stored in these two media are summarized in Table 4 for comparison.

TABLE 4

Comparison of the efficacy of the present isotonic medium and Optisol for donor corneal storage

| Parameters | Storage Duration (days) | Storage Media | |
| --- | --- | --- | --- |
| | | present isotonic medium | Optisol |
| In Vivo Deturgescence | 7 | 16.2 ± 8.5 | 0.51 ± 0.06 |
| (μm/hr) | 11 | 1.4 ± 0.2 | 0.42 ± 0.07 |
| Half-time for Donor | 7 | 2.4 ± 1.8 | 133.2 ± 14.3 |
| Cornea to Return | 11 | 33.6 ± 14.4 | 311.2 ± 60.0 |
| to Normal Thickness | | | |
| After Grafting (hours) | | | |

Four corneas are used in each experiment

The results show that the present isotonic medium is significantly better than Optisol in terms of preserving corneal tissue viability and endothelial fluid pump function.

Thus, the experiments described in Examples 1, 2, and 3 demonstrate that the present invention is unique and effective. It is clearly evident that the present composition is particularly useful as an energy source for peripheral tissues to sustain viability and to perform physiological and biological functions.

While the invention has been described with respect to certain specific embodiments, it will be appreciated that many changes and modifications may be made by those skilled in the art without departing from the spirit of the invention. It is intended, therefore, by the appended claims to cover all such modifications and changes as fall within the true spirit and scope of the invention.

What is claimed is:

1. An isotonic aqueous composition comprising,

| | |
| --- | --- |
| D,L-Sodium β-Hydroxybutyrate | 5–30 mM |
| Dibasic Sodium Phosphate | 1.5–6.0 mM |
| Monobasic Sodium Phosphate | 0.3–1.2 mM |
| Sodium Citrate | 1.2–7.2 mM |
| Calcium Chloride | 0.5–2.0 mM | wherein $HPO_4^{-2}$, $Ca^{2+}$ and citrate are kept at a defined ratio where the product of $[HPO_4^{-2}]$ $[Ca^{2+}]$ ranges from 1.2 to 3.2, the concentration of citrate ranges from 50% to 120% the concentration of $[HPO_4^{-2}]$ and $[HPO_4^{-2}]/[H_2PO_4^{-1}]$ ratio is 5:1.

2. The isotonic aqueous composition of claim 1 further comprising,

| | |
| --- | --- |
| Potassium Chloride | 5–20 mM |
| Sodium Chloride | 95–135 mM |
| Magnesium Chloride | 0.5–1.5 mM |
| Calcium Chloride | 0.5–2.0 mM. |

3. An isotonic aqueous composition consisting essentially of,

| | |
| --- | --- |
| D,L-Sodium β-Hydroxybutyrate | 5–39 mM |
| Glucose | 2–10 mM |
| Sodium Glucuronate | 5–20 mM |
| Dextran | 4–15 (%) |
| Pre-formulated essential Amino Acids, Vitamins and Other components | (full strength) |
| Sodium Hepes | 10–50 mM |
| Potassium Chloride | 5–20 mM |
| Sodium Chloride | 60–100 mM |
| Dibasic Sodium Phosphate | 1.5–6.0 mM |
| Monobasic Sodium Phosphate | 0.3–1.2 mM |
| Magnesium Chloride | 0.5–1.5 mM |
| Calcium Chloride | 0.5–2.0 mM. |

4. A process for preparing a sterile isotonic aqueous solution suitable for use as an irrigating solution comprising, dissolving and thoroughly mixing a composition having the following composition,

| | |
| --- | --- |
| D,L-Sodium β-Hydroxybutyrate | 5–30 mM |
| Potassium Chloride | 5–20 mM |
| Sodium Chloride | 60–100 mM |
| Dibasic Sodium Phosphate | 1.5–6.0 mM |
| Monobasic Sodium Phosphate | 0.3–1.2 mM |
| Sodium Citrate | 1.2–7.2 mM | in deionized, double-distilled and degassed $H_2O$, adjusting the pH to 7.3–7.4, adding $CaCl_2$ and $MgCl_2$ to form an isotonic solution in the range from 290 to 315 mOsM, readjusting the pH to 7.3–7.4, filtering the solution through 0.22 μm membrane, sealing the solution under conditions which insure a complete elimination of $O_2$ from the solution to protect β-hydroxy butyrate from oxidation and to extend shelf-life, sterilizing the solution by autoclave or showers of superheated water, and rapidly cooling the solution until any precipitation disappears.

5. The sterile isotonic aqueous solution produced by the process of claim 4.

6. The composition of claim 1 wherein citrate is replaced with isocitrate in the range from 1.2 to 7.2 mM.

7. The composition of claim 1, wherein the β-hydroxybutyrate is selected from the group consisting of D-isomer, a D- and L- racemic mixture and a D- and L-isomer mixture.

8. The composition of claim 1 wherein all or a portion of β-hydroxybutyrate is replaced with one 5 or more ketogenic amino acids selected from the group consisting of leucine, phenylalanine, lysine, tyrosine and tryptophan, at concentrations from 0.1 to 5 mM.

9. The composition of claim 1 wherein glucose is present in a concentration from 2 to 10 mM.

10. The composition of claim 1 wherein the composition further comprises a polymer selected from the group consisting of dextran, sodium hyaluronate, hydroxypropyl methylcellulose, polyvinyl pyrrolidone and methylcellulose with a molecular mass ranging from 0.5 to $2\times10^6$ daltons and is present in amounts sufficient to form a highly viscous solution for application on the external surface of the eye and in the anterior chamber.

11. A slow-release drug delivery vehicle prepared by thoroughly mixing the composition of claim 1, medication and polymers selected from the group consisting of dextran, sodium hyaluronate, hydroxypropyl methylcellulose, polyvinyl pyrrolidone and methylcellulose with a molecular mass ranging from 0.5 to $2\times10^6$ daltons in amounts sufficient to form a highly viscous solution.

12. The composition of any one of claims 10 and 11, wherein the concentration of polymers is 1%, or in the range from 0.1% to 5%.

13. The composition of any one of claims 10 and 11, wherein the medication includes antibiotics, steroids, and/or those drugs suitable for treating eye diseases, with strength increased by 2 to 5 fold for application on the external surface of the eye and in the anterior chamber.

14. An efficient antibiotics ointment or cream prepared by combining the composition of claim 1 and antibiotics ointment or cream for external applications suitable for wound healing, which is effective to meet requirements of dermal and ocular tissues for efficient physiological and biochemical functions with concurrent suppression of lactate production and accumulation.

15. An enriched cream or lotion prepared by combining the composition of claim 1 and a cream or lotion for enhanced dermal cares, which is effective to meet requirements of dermal tissues for efficient physiological and biochemical functions with concurrent suppression of lactate production and accumulation.

16. An isotonic cornea storage medium prepared by thoroughly mixing the composition of claim 1, 10 mM sodium glucuronate, polymers, 30 mM Hepes buffer, and preformulated minimum essential amino acids, vitamins and other components of Medium 199, with the omission of ascorbate and a reduction in NaCl concentration so that the resulting medium is isotonic in the range from 290 to 315 mOsM, and has a pH ranging from 7.1 to 7.6, and sterilized by filtration through 0.22 μm filter membrane.

17. An cornea storage medium prepared by thoroughly mixing the composition of claim 1, 10 mM sodium glucuronate, polymers, 30 mM Hepes buffer, and preformulated minimum essential amino acids, vitamins and other components of Medium 199, with the omission of ascorbate and a reduction in NaCl concentration so that the resulting medium is hypertonic in the range from 315 to 380 mOsM, and has a pH ranging from 7.1 to 7.6, and sterilized by filtration through 0.22 μm filter membrane.

18. The isotonic cornea storage medium of any one of claims 16 and 17, wherein glucuronate is replaced with a member of the group selected from N-acetyl glucosamine, gluconate, glucarate, mannuronate, and galacturonate.

19. The isotonic cornea storage medium of any one of claims 16 and 17, wherein polymers has a concentration in the range from 0.5 to 10% and is selected from the group consisting of dextran, sodium hyaluronate, hydroxypropyl methylcellulose, polyvinyl pyrrolidone and methylcellulose with a molecular mass ranging from 4 to $7\times10^4$ daltons in amounts sufficient to effectively suppress swelling of stored cornea.

20. The isotonic cornea storage medium of any one of claims 16 and 17, wherein the pre-formulated amino acids and vitamins are replaced by a member of the group selected from Eagle's, Dubelcco's and Daniel's media.

21. An efficient solution for storage and preparation of donor tissues for organ transplantation and for topical applications prepared by thoroughly mixing the composition as in claims 1, 16 or 17 and a synergistically effective mixture of 0.1 mg/ml dialyzed fetal bovine retinal extract (as the source of vascular endothelial growth factor), 10 μM uridine, 0.5 μM thymidine and 3 mg/ml dialyzed fetal bovine serum (as the source of serum-derived factor), by reducing NaCl concentration to adjust osmolarity the range of 290 to 315 mOsM, and by filtering through 0.22 μm filter membrane to sterilize the solution.

22. An isotonic aqueous medical composition suitable for autoclave sterilization without caramelization precipitation comprising,

| | |
|---|---|
| Dibasic Sodium Phosphate | 1.5–6.0 mM |
| Monobasic Sodium Phosphate | 0.3–1.2 mM |
| Sodium Citrate | 1.2–7.2 mM |
| Calcium Chloride | 0.5–2.0 mM | wherein $HPO_4^{-2}$, $Ca^{2+}$ and citrate are kept at a defined ratio where the product of $[HPO_4^{-2}]$ $[Ca^{2+}]$ ranges from 1.2 to 3.2, and the concentration of citrate ranges from 50% to 120% the concentration of $[HPO_4^{-2}]$ and $[HPO_4^{-2}]/[H_2PO_4^{-1}]$ ratio is at 5:1.

23. In an isotonic physiologically compatible medical composition containing at least phosphate, calcium ions and alkali metal citrate wherein the improvement comprises the presence of $HPO_4^{-2}$, $Ca^{2+}$ and citrate ions at a defined ratio where the product of ranges from 1.6 to 3.2 and the concentration of citrate ranges from 50% to 120% the concentration of thereby preventing caramelization and precipitation when autoclaved.

* * * * *